United States Patent [19]
Yeal

[11] Patent Number: 6,023,784
[45] Date of Patent: Feb. 15, 2000

[54] HEADWEAR WITH DUAL VISORS

[75] Inventor: Jung Jin Yeal, Gyungki-do, Rep. of Korea

[73] Assignee: Il Sung International Co., Ltd., Seoul, Rep. of Korea

[21] Appl. No.: 09/282,020

[22] Filed: Mar. 29, 1999

[30]     Foreign Application Priority Data

Apr. 24, 1998 [KR] Rep. of Korea ..................... 98-14610
Mar. 15, 1999 [KR] Rep. of Korea ..................... 99-8647

[51] Int. Cl.⁷ ..................................................... A42B 3/18
[52] U.S. Cl. ......................................................... 2/9; 2/12
[58] Field of Search ............................... 2/9, 12, 15, 424, 2/10, 195.1

[56]     References Cited

U.S. PATENT DOCUMENTS 3,686,690   8/1972   Webb .............................................. 2/9

*Primary Examiner*—Diana Oleksa
*Attorney, Agent, or Firm*—Abelman, Frayne & Schwab; Stewart J. Fried

[57]     ABSTRACT

A cap with a hinged ultraviolet ray visor is disclosed. The ultraviolet ray visor or a main visor is made of a transparent or translucent material capable of intercepting ultraviolet rays, and is rotatably attached to both sides of an elastic head band at both ends thereof by two joint pins. In an embodiment, an auxiliary visor is attached to both sides of the head band at both ends thereof by the two joint pins so as to be positioned between the head band and the main visor. The angular position of the main visor relative to the head band is easily adjusted by a user when necessary.

5 Claims, 5 Drawing Sheets

HEADWEAR WITH DUAL VISORS

BACKGROUND OF THE INVENTION

1. Field of the Invention

The present invention relates, in general, to caps used for being worn on the head to protect the head from strong sunlight and, more particularly, to a cap with a hinged ultraviolet ray visor, said visor being made of an anti-ultraviolet material and being hinged to a head band, thus allowing a user to easily change the angular position of the visor relative to the head band when necessary.

2. Description of the Prior Art

While participating in an outdoor sport, such as cycling or jogging, or viewing an outdoor game, such as football or baseball, under strong sunlight, the eyes may be exceedingly stimulated by strong light from the sun, thus momentarily losing sight. This inhibits participants or spectators from achieving clear, visual perception. Particularly, when the head is directly exposed to strong light from the sun for a lengthy period of time, facial skin may be seriously damaged and suffer from undesired pigmentation, freckles, sunburn and/or skin cancers. In recent years, the ozonosphere has been deteriorated at several areas due to serious air pollution and this results in a remarkable increase in the amount of ultraviolet rays radiated onto the ground along with sunlight. Skin maladies, such as skin cancers caused by the ultraviolet rays, thus become worse.

It is necessary for people to protect the eyes and skin from ultraviolet ray-laden strong light from the sun. This may be accomplished by caps and/or sunglasses. Such caps typically have a visor or a projecting front brim designed to protect the face from strong sunlight, while sunglasses are designed to protect the eyes. In addition, several types of anti-ultraviolet skin creams capable of protecting the skin from ultraviolet rays have been proposed and widely used. Such a skin cream is directly applied on the skin.

However, known anti-ultraviolet skin creams are problematic in that they may undesirably cause a skin malady or a allergic reaction to chemicals or the ingredients of the creams. Another problem of the above skin creams resides in that they may cause water pollution in swimming pools, and so use of the skin creams is thus restricted in such places. This is inconvenient to users of such skin creams.

In comparison with the anti-ultraviolet skin creams, caps and sunglasses are more convenient to users since they are more easily and conveniently used outdoors without being restricted by location or place of use. However, known sunglasses are only designed to protect the eyes from reflected strong sunlight, but are lacking any means for protecting the face from ultraviolet rays.

On the other hand, known caps are problematic in that the visors are fixed to the front portion of the head band, thus failing to effectively protect the face from strong light from the sun since the radiation angle of the sunlight is continuously variable. When a cap of the known variety is worn on the head of a user while participating in a speedy sport, such as cycling or roller blading, the visor of the cap may be resisted by a high wind, thus unexpectedly removing the cap from the head. The known caps, with such fixed visors, thus reduce activity of the user while participating in such a speedy sport. This forces the user to reset the position of the cap on the head from a front visor position to a rear visor position prior to being involved in the sport. However, the caps in such a rear visor position regrettably fail to protect the face from strong sunlight laden with ultraviolet rays.

SUMMARY OF THE INVENTION

Accordingly, the present invention has been made keeping in mind the above problems occurring in the prior art, and an object of the present invention is to provide a cap, which has an ultraviolet ray visor hinged to a head band, the visor thus allowing a user to easily change the angular position of the visor relative to the head band in accordance with both the variable radiation angle of sunlight and a posture of the user, and thereby almost completely protecting the face from strong sunlight regardless of the sunlight radiation angle or the user's posture.

Another object of the present invention is to provide a cap, of which the visor is designed to be movable in angular position relative to the head band, thus being almost completely free from being resisted by a high wind when a user participates in a speedy sport, such as cycling or roller blading.

In order to accomplish the above objects, the preferred embodiment of the present invention provides a cap, comprising: an elastic head band; and a main visor rotatably attached to both sides of the head band at both ends thereof by the pins, thus being angularly movable upwardly and downwardly relative to the head band. Additionally the cap further comprises an auxiliary visor exteriorly attached to both sides of the head band at both ends thereof by two joint pins, thus being exteriorly positioned along a front portion of the head band and between the head band and the main visor.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
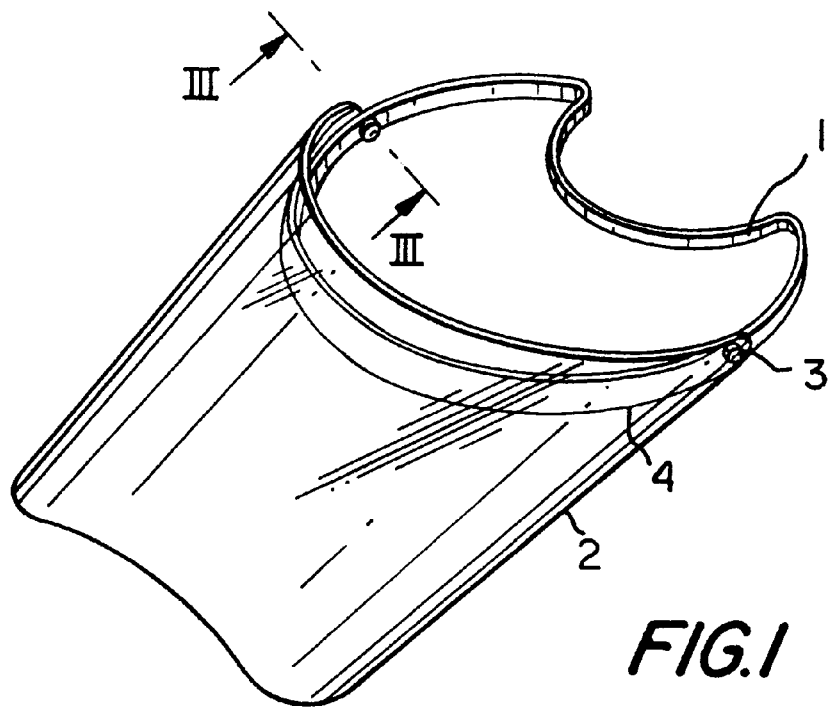
FIG. 1 is a perspective view of a cap with a hinged ultraviolet ray visor in accordance with the primary embodiment of the present invention.
Figure 3:
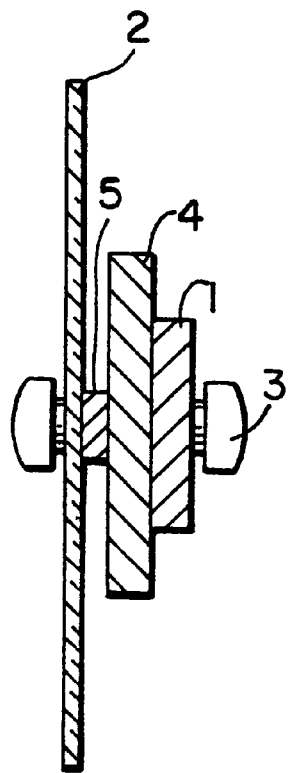
FIG. 3 is a sectional view taken along the line III—III of FIG. 1, showing a hinged joint between the head band and the visor of the cap.
Figure 2:
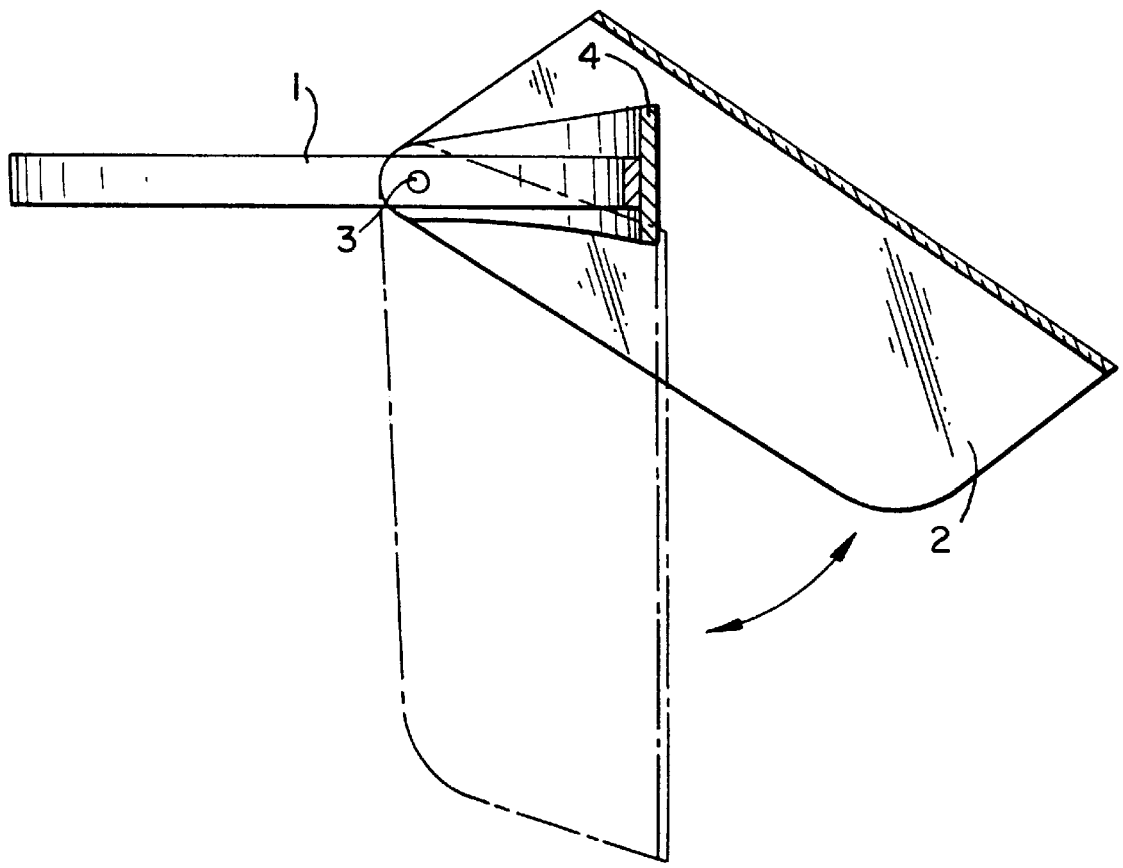
FIG. 2 is a side view, showing an adjustment of the angular position of the above visor relative to a head band in the cap of FIG. 1.

FIGS. 1 to 3 show the construction and operation of a cap with a hinged ultraviolet ray visor in accordance with the primary embodiment of this invention. As shown in the drawings, the cap of this invention comprises a head band 1, a main visor 2, two joint pins 3, and an auxiliary visor 4.

The head band 1 is a conventional head band, which is sized to be appropriately fitted around the head of a user and preferably has an elasticity capable of preventing an unexpected removal of the head band 1 from the head.

The main visor 2, made of a transparent or translucent material, is attached to the head band 1 at both ends thereof by said pins 3. The above main visor 2 is rotatable around the joint pins 3 at an angle, thus being angularly movable upwardly and downwardly relative to the head band 1.

The above main visor 2 is preferably made of a transparent or translucent anti-ultraviolet material, more preferable, a polycarbonate material capable of intercepting ultraviolet rays. The main visor 2 thus may be a so-called ultraviolet ray visor. When the main visor 2 is exceedingly thick, the elasticity of the visor 2 is too high, thus spoiling the curved appearance of the visor 2. On the other hand, when the visor 2 is exceedingly thin, the structural strength of the visor 2 is too low, thus allowing the visor 2 to be unexpectedly broken. Therefore, it is preferable to set the thickness of the visor 2 to a range of 0.3 mm–0.5 mm. In order to prevent the visor 2 from being unexpectedly broken due to friction or impact, the outside edge of the visor 2 is preferably covered with a cloth.

The auxiliary visor 4 is attached to both sides of the head band 1 at both ends thereof by the two joint pins 3 in a way such that the auxiliary visor 4 is exteriorly positioned along the front portion of the head band 1 and is positioned between the head band 1 and the main visor 2. The above auxiliary visor 4 has a width larger than that of the head band 1 and is preferably fixed so as to be prevented from moving relative to the head band 1.

As best seen in FIG. 2, when the main visor 2 is rotated downwardly around the pins 3, the rotation is strictly controlled around the joint pins 3 at an angle. Furthermore, when the main visor 2 is in a vertical position, the auxiliary visor 4 stops the middle portion of the main visor's inside edge at its lower edge, thus preventing the main visor 2 from unexpectedly further moving downwardly. That is, the auxiliary visor 4 restricts the rotating angle of the main visor 2.

As described above, the main visor 2 is rotatably attached to both sides of the head band 1 by the joint pins 3, with the auxiliary visor 4 being positioned between the head band 1 and the main visor 2. In such a case, each of the pins 3 passes through the main visor 2, the auxiliary visor 4 and the head band 1 in order.

A high elastic bushing 5 is preferably fitted over each of the pins 3 at a position between the main and auxiliary visors 2 and 4 as shown in FIG. 3. The above bushing 5 biases the main visor 2 outwardly, thus allowing the main visor 2 to have a smoothly curved configuration.

Figure 4:
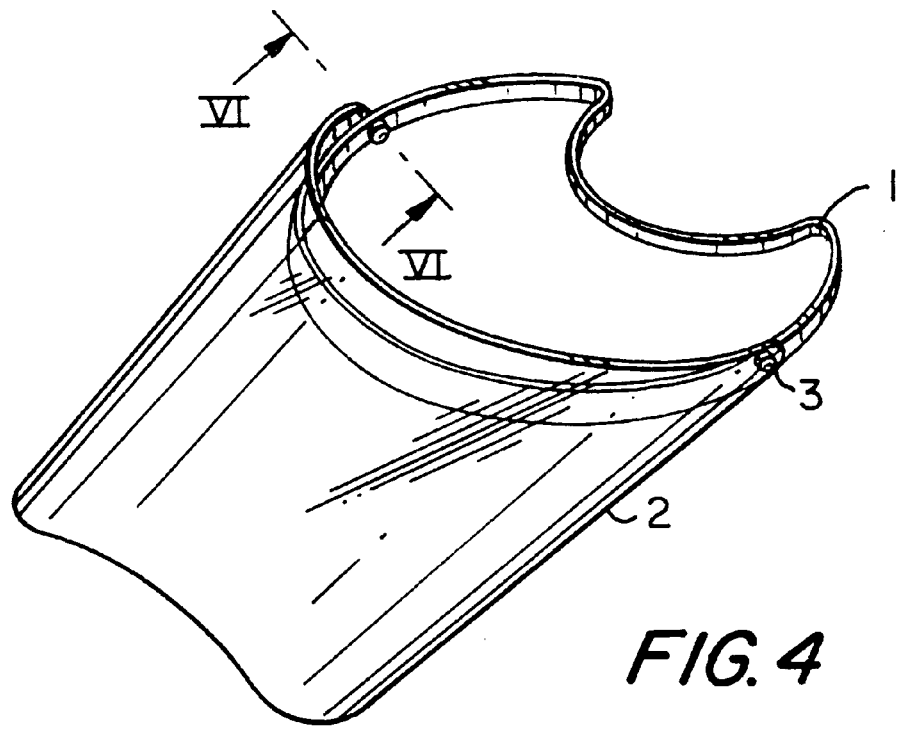
FIG. 4 is a perspective view of a cap with a hinged ultraviolet ray visor in accordance with the secondary embodiment of the present invention.
Figure 6:
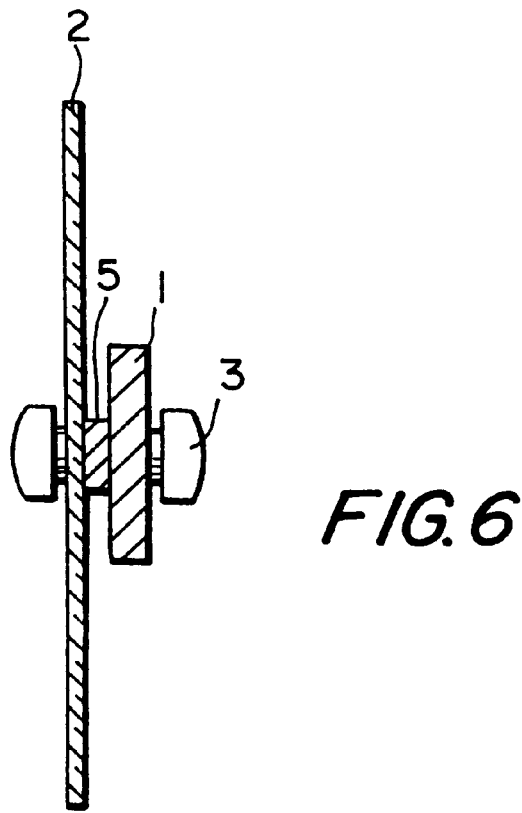
FIG. 6 is a sectional view taken along the line VI—VI of FIG. 4, showing a hinged joint between the head band and the visor of the cap.
Figure 5:
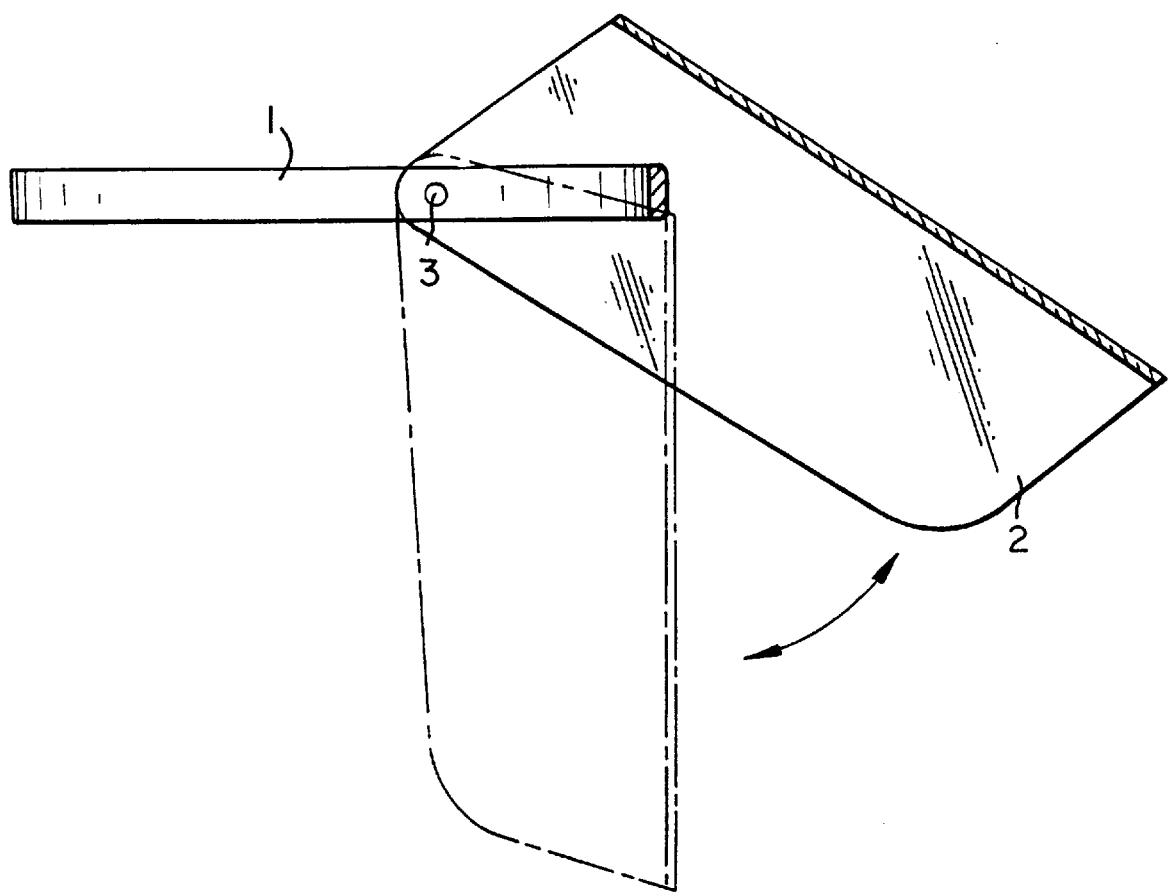
FIG. 5 is a side view, showing an adjustment of the angular position of the above visor relative to a head band in the cap of FIG. 4.

FIGS. 4 to 6 show the construction and operation of a cap with a hinged ultraviolet ray visor in accordance with the second embodiment of this invention. As shown in the drawings, the cap of the second embodiment of this invention comprises a head band 1, a main visor 2 and two joint pins 3.

The main visor 2, made of a transparent or translucent polycarbonate material, is attached to the head band 1 at both ends thereof by side pins 3. The above main visor 2 is rotatable around the joint pins 3 at an angle, thus being angularly movable upwardly and downwardly relative to the head band 1. In such a case, each of the pins 3 passes through the main visor 2 and the head band 1 in order.

As best seen in FIG. 5, when the main visor 2 is rotated downwardly around the pins 3, the rotation is strictly controlled around the joint pins 3 at an angle, even though there is no auxiliary visor 4.

A high elastic bushing 5 is preferably fitted over each of the pins at a position between the main visor 2 and the head band 1 as shown in FIG. 6. The above bushing 5 biases the main visor 2 outwardly, thus allowing the main visor 2 to have a smoothly curved configuration.

The operational effect of the above cap will be described hereinbelow.

When the cap is used in days of agreeable sunlight, the main visor 2 is manually controlled to have a generally horizontal position wherein the main visor 2 is slightly tilted downwardly relative to the head band 1 as shown in FIGS. 2 and 5.

In such a case, the middle portion of the main visor's inside edge is positioned approximate to the upper front portion of the head while being spaced apart from the upper edge of the auxiliary visor 4 or the head band 1. On the other hand, the middle portion of the main visor's outside edge is positioned to be almost completely aligned with the line of sight.

When wearing the cap on the head as described above, the main visor 2 can effectively protect the face from ultraviolet rays laden in the agreeable sunlight.

When the cap is used in days of strong sunlight or while participating in a speedy sport, such as cycling or roller blading, the main visor 2 is manually controlled to have a vertical position wherein the visor 2 is almost perpendicular to the head band 1.

In case of a cap having the auxiliary visor 4, the middle portion of the main visor's inside edge is brought into the lower edge of the auxiliary visor 4, thus being stopped by said auxiliary visor 4. On the other hand, the middle portion of the main visor's outside edge is positioned around the chin. The face is thus shielded by the main visor 2, and so the face is almost completely protected from ultraviolet rays laden in sunlight. The main visor 2 in the vertical position is almost completely free from being resisted by a high wind when a user participates in a speedy sport, such as cycling or roller blading. The main visor thus improves activity of the user while performing such a speedy sport.

Those skilled in the art will appreciate that various modifications, additions and substitutions are possible, without departing from the scope and spirit of the invention.

That is, it is possible to change the configuration of both the head band and the joint pins.

Figure 7:
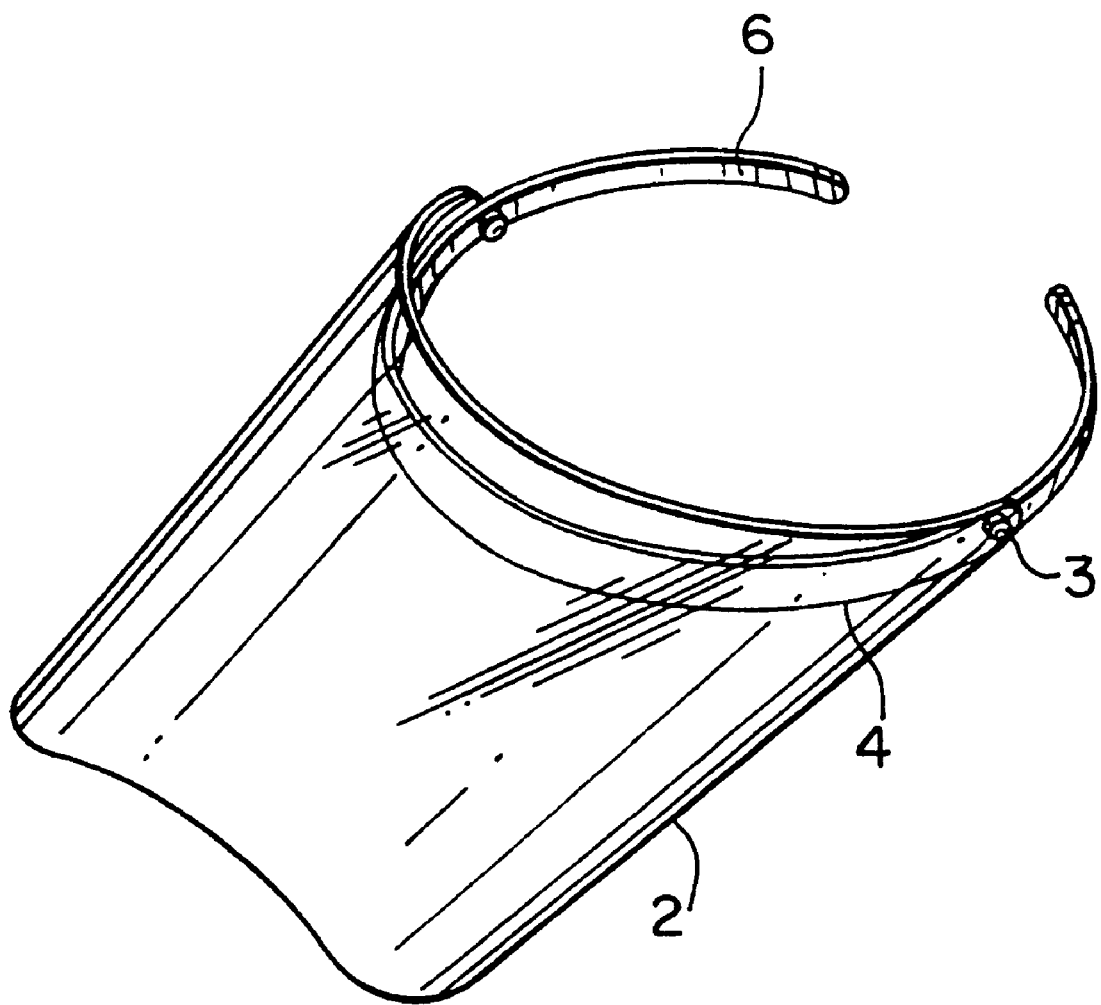
FIG. 7 is a perspective view of a cap with a hinged ultraviolet ray visor in accordance with the third embodiment of the present invention.

For example, the head band of the cap may be formed as a well-known C-shaped head band 6 as shown in FIG. 7. Such a C-shaped head band 6 allows a user to more easily wear the cap on the head. In addition, a fastening means may be provided at both ends of the C-shaped head band, thus fastening the two ends of the cap fitted over the head. For example, both ends of the C-shaped head band may be formed as strips respectively provided with hook and pile parts of a Velcro.

In an effort to allow a user to more precisely adjust the angular position of the main visor relative to the head band, a gear mechanism may be installed at the junction between the main visor and each joint pin.

As described above, the present invention provides a cap with a hinged ultraviolet ray visor. The ultraviolet ray visor or a main visor is made of a transparent or translucent material, and is rotatably attached to both sides of an elastic head band at both ends thereof by two joint pins. It is thus possible for a user to easily adjust the angular position of the main visor relative to the head band when necessary. In days of strong light from the sun, the position of the main visor relative to the head band may be manually adjusted to a vertical position wherein the visor covers and shields the face. The main visor in such a position almost completely protects facial skin from ultraviolet rays laden in sunlight. The main visor in the vertical position is almost completely free from being resisted by a high wind when a user participates in a speedy sport, such as cycling or roller blading. The cap of this invention thus improves activity of the user while participating in such a speedy sport. When an auxiliary visor is exteriorly printed with advertising characters, symbols, figures, and the like, the cap has a collateral advantage of accomplishing a desired advertising effect. The hinged main visor of this invention may be preferably used as a rooting instrument. That is, when a party of rooters cheer a team while wearing the caps of this invention with the main visors being vertically positioned, the rooters may show a strong image.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A cap, comprising:

an elastic head band;

an auxiliary visor exteriorly attached to both sides of said head band at both ends thereof by two joint pins, thus being exteriorly positioned along a front portion of the head band; and a main visor rotatably attached to both sides of the head band at both ends thereof by said pins, with the auxiliary visor being positioned between the head band and the main visor, said main visor being rotatable around the pins at an angle, thus being angularly movable upwardly and downwardly relative to the head band.

2. The cap according to claim 1, wherein said main visor is made of a light transmissive material capable of intercepting ultraviolet rays.

3. The cap according to claim 1, wherein a high elastic bushing is fitted over each of said pins at a position between the main and auxiliary visors, thus biasing the main visor outwardly.

4. The cap according to claim 1 wherein said main visor is made of a transparent polycarbonate material capable of intercepting ultraviolet rays.

5. The cap according to claim 1 wherein said main visor is made of a translucent polycarbonate material capable of intercepting ultraviolet rays.

* * * * *

UNITED STATES PATENT AND TRADEMARK OFFICE
CERTIFICATE OF CORRECTION

PATENT NO.    : 6,023,784
DATED         : February 15, 2000
INVENTOR(S)   : Jin Yeal Jung It is certified that error appears in the above-identified patent and that said Letters Patent is hereby corrected as shown below:

<u>Title page,</u>
Item [75], correct the inventor's name to read Jin Yeal Jung.

Signed and Sealed this

Eighth Day of January, 2002

Attest:

JAMES E. ROGAN
*Attesting Officer*      *Director of the United States Patent and Trademark Office*